Figure 2:
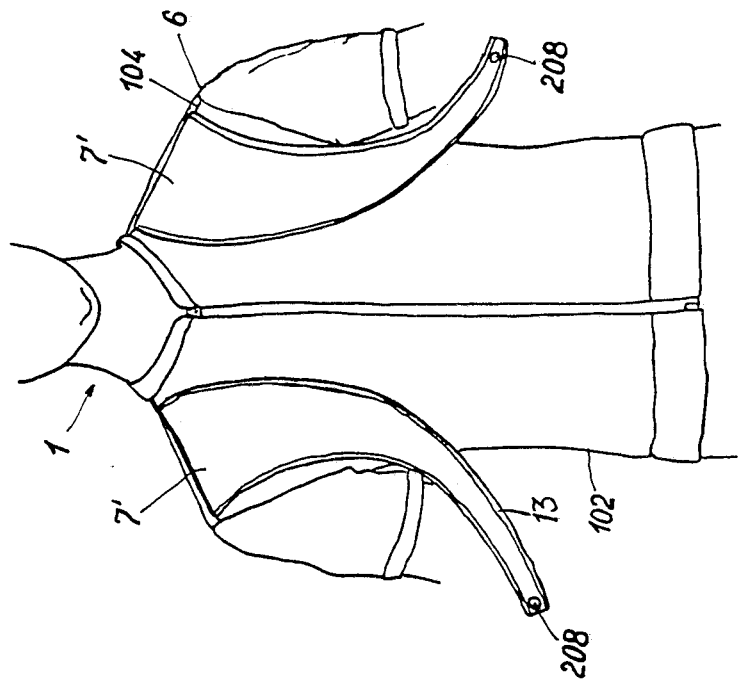

United States Patent [19]

Benckhuijsen

[11] Patent Number: 4,785,803

[45] Date of Patent: Nov. 22, 1988

[54] SHOULDER TRUSS

[75] Inventor: Gerrit J. Benckhuijsen, Schaan, Liechtenstein

[73] Assignee: Temova Establishment, Schaan, Liechtenstein

[21] Appl. No.: 19,592

[22] PCT Filed: Jun. 19, 1986

[86] PCT No.: PCT/EP86/00361

§ 371 Date: Feb. 20, 1987

§ 102(e) Date: Feb. 20, 1987

[87] PCT Pub. No.: WO86/07534

PCT Pub. Date: Dec. 31, 1986

[30] Foreign Application Priority Data

Jun. 20, 1985 [CH] Switzerland .................. 02606/85

[51] Int. Cl.$^4$ .............................................. A61F 5/04
[52] U.S. Cl. ...................................... 128/87 R; 128/78; 2/45
[58] Field of Search ............... 2/44, 45; 128/99, 78, 128/100, 101, 95, 781, DIG. 19, 87 R, 87 B; 450/1, 2, 3

[56] References Cited

U.S. PATENT DOCUMENTS

| | | | |
|---|---|---|---|
| 1,075,348 | 10/1913 | Fritsch | 128/DIG. 19 X |
| 2,828,737 | 4/1958 | Hale | 128/78 |
| 3,116,735 | 1/1964 | Geimer | 128/78 X |
| 3,141,456 | 7/1964 | Meek | 128/78 X |
| 3,548,818 | 12/1970 | Kaplan | 128/78 |
| 3,783,879 | 1/1974 | Stalder | 128/570 |
| 3,856,004 | 12/1975 | Cox | 128/87 R |
| 3,857,388 | 12/1974 | Frankel | 128/87 R |
| 3,897,776 | 8/1975 | Gaylord, Jr. | 128/87 R |
| 4,336,807 | 6/1982 | Benckhuijsen | 128/379 |
| 4,444,191 | 4/1984 | Harned | 2/45 X |
| 4,641,642 | 2/1987 | Williams, Jr. | 128/78 X |
| 4,644,939 | 2/1987 | Coleman | 128/78 |

FOREIGN PATENT DOCUMENTS

| | | |
|---|---|---|
| 1261918 | 3/1963 | France . |
| 2368263 | 5/1978 | France . |
| 758255 | 1/1984 | France . |
| 641344 | 2/1984 | Switzerland . |

OTHER PUBLICATIONS

GMA Heft 27 vom 1.7.1976 Klasse A 61-5/05 76 06 753 5.3.1976; GMA Heft 23 vom 7.6.1984 Klasse A 61-5/01 GM 84 07 242 AT 09.03.84; GMA Heft 20 vom 19.5.1982 Klasse A 47-A 61 F-5/37 GM 80 33 025. Swiss Temova Establishment dated Jun. 20, 1985—Patent Search EPO.

Primary Examiner—Robert A. Hafer
Assistant Examiner—Kevin G. Rooney
Attorney, Agent, or Firm—Cushman, Darby & Cushman

[57] ABSTRACT

An elastic shoulder truss (3) possessing a rear portion (9) which covers at least both shoulder-blades. The tension of the material transversely across the back and longitudinally along the tension straps (7) when measured with a 10% elongation on 5 cm wide and 10 cm long straps is between about 400 g and about 1200 g, preferably 500 g to 800 g, at a displacement speed of 5 cm per minute. When measured in the same conditions the tension of the material longitudinally over the back and transversely across the tension straps is between about 200 g and about 500 g, preferably 300 g to 400 g. In this way, the shoulder joint (6) of the carrier (1) is enclosed, for example, in a socket-like cavity (6) which is formed of the back portion (9) and the widened application area (7') of a tension strap (7) connected with the back portion by means of the shoulder seam (5). Both tension straps (7) are secured to the back section (9) of the carrier (1), e.g. to the side seam (12) under the armpit (4). It is advantageous if the truss (3) is worn on an under-shirt (2) and/or covered by an over-shirt (10).

13 Claims, 2 Drawing Sheets

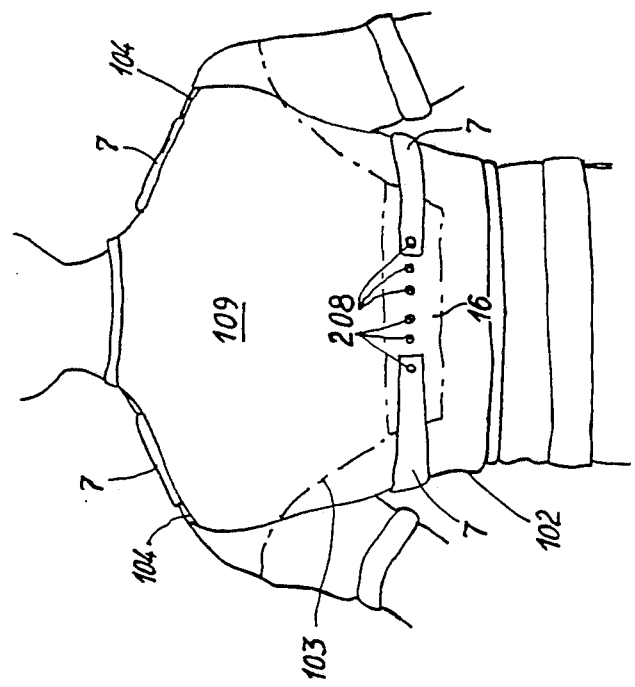
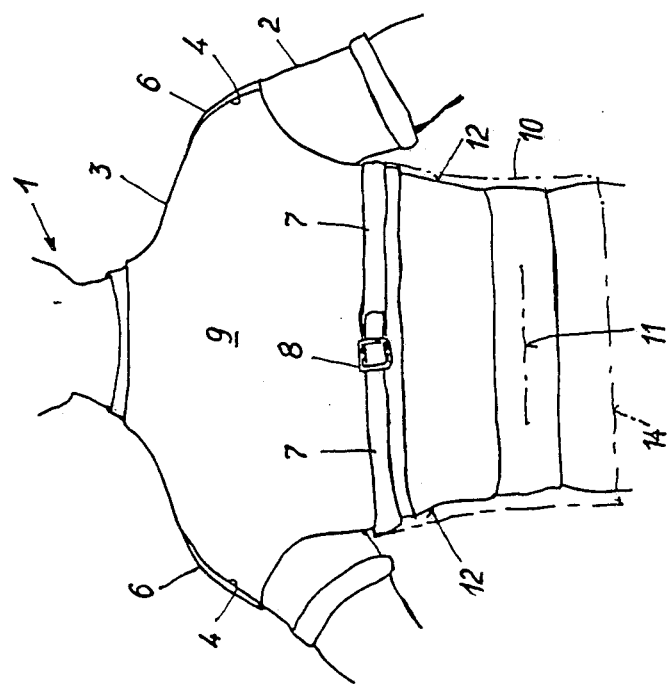

SHOULDER TRUSS

The invention relates to a shoulder bandage according to the part of claim 1 describing the state of the art.

To date, such bandages were used primarily in collar bone fractures, and are known e.g. from U.S. Pat. Nos. 3,856,004 and 3,857,388. They force the wearer to assume a straight posture, his mobility being extremely limited because of the pull bands being only slightly stretchable in the manner of backpack-carrying straps and usually arranged very near the neck area.

In this context the shoulder belt according to U.S. Pat. No. 3,548,818 is of only little help because of the large-area back part, as well as the pull bands, can be stretched essentially only in the longitudinal direction, and hence affect only a limited number of movements or degrees of freedom of the wearer.

For example, an elastic vest with support collar which can be used for therapeutic purposes has also become known from CH-A-641344. In this case, however, the principal objective is the support in the cervical region, or the effect of heat in the shoulder joint. In contrast to the aforementioned "static" collarbone bandages, and also to the forementioned shoulder belt, the invention proceeds from quite different problematics that are to be met by the aid of a shoulder bandage with "dynamic" action on all sides. Namely, to date a shoulder bandage which has gladly been worn, and which still achieved its intended effect, did not exist.

The progress of civilization has led to a highly developed, predominately sitting human being who has becomed accustomed to sitting in a crooked position, because of which the thoracic girdle, especially the acromio-clavicular joint is overstressed. The spinal column as the supporting member of the body is used only partially, while other parts of the trunk, which were oridinally intended for other functions, such as the breastbone, must take over functions as supporting and holding functions of the truck. Since in the relaxed sitting position ("sternal tensioning posture") the breast kyphosis is intensified and the lumbar lordosis is cancelled, both spinal column sections form a uniform kyphotic arc; in contrast to the position of the thorax when standing and walking, the sternal joints are overstressed.

During sitting the axial weight on the spinal column is converted into flexure; the center of gravity line is displaced ventrally, and the weight of the head and the thoracic girdle and the arms is transmitted predominately to the breastbone—which is not without its effects on the position of the cervical vertebral column and on the joints of the thoracic girdle which are thereby irritated. The musuclature is reflex-tensioned and pain signals are sent to the spinal marrow and the brain stem, which transform the signal of the incorrect stressing of the breastbone joints into an orderly and effective musculatory resistance intended to relieve for releiving the tension of the aching joints. The corresponding muscles are innervated (e.g. musculus sternocleidomastoideus, musculi scaleni, extensor of the back), which can lead to an overstressing of this musculature, and consequently to extensive pains in the entire region of the thoracic spine up to the back part of the head.

In the treatment of persistent cervical syndrome, shoulder-arm syndrom and thoracal syndrome these mechanisms must also be taken into account. They are the result of secondary side effects of a nociceptive somatomotoric blocking effect having its origin in the pain sensors (nociceptors) of the affected articular capsules, tendom attachments, of the periosteum and other tissues. It is the expression of reflectory mechanisms that are available to the organism to spare the irritated tissue.

Based on these findings the invention has as its objective the improvement of the supporting action in the shoulder region and the counteraction of the sternal stressing posture by a continuous and adjustable pull in the area of the shoulder belt. This is accomplished by the shoulder joint bandage according to the present invention developed after thorough study of the locomotion system and its pathological changes, as well as the effects thereof in the form of painful syndromes by the characteristics of claim 1—preferably in connection with the characteristics stated in one or more subclaims.

In contrast with the aforementioned collarbone bandage the bandage according to the present invention achieves an effect of a very different nature, and it has proven that not only can a special supporting action thereby be achieved in the region of the shoulder joint, but that the wearer is gently forced to assume a straight posture without being obstructed in his mobility.

For this reason the spaded part on the end of the front pull belt is very important because it brings the upper arms into a slightly spread-apart position. The distance of the pull band fixation of the back part from the shoulder seam also has a certain significance. Here, the forces must be transmitted to the back part in an appropriate manner. For the medical specialist, however, this is a magnitude that can be determined in a particular case.

The two pull bands unite their corrective action dorsally in the area of the breast kyphosis peak. The center-of-gravity line extending in front of the thoracic spine and the lumbar vertical column in the case of sternal stressing posture is normalized by dorsal displacement; the tension on the sternoclavicular joints, the costosternal connections and the shoulder joints is relieved. The mechanical irritation of the ligamentous apparatus and joints, and the pain emanating therefrom to the pain sensors of this region, are eliminated; the arthro-tendomyotic reflex mechanism is interrupted.

The tension on the musculature that is overstressed on sternal stressing posture (especially m. sternocleidomatoideus, m. scaleni, erector spinae musculature) is relieved; conversely, extensions of the m. pectoralis minor and m. pectoralis major is achieved. Irritated conditions with associated pains in the costosternal connections, as well as in the clavicolosternal joints, recede.

The bandage according to the present invention is therefore a bandage that can expediently be used to treat shoulder pains, especially for the treatment of the cervical syndrome and the thoracal syndrome.

The widening of the pull bands, e.g. to the width of the shoulder seam is of advantage because this enables the reminder function of the bandage to be exercised more gently, so that the desire of the patient to wear the bandage is increased. Namely, many therapeutic means cannot unfold their action because they are either not applied by the patient, or done so only to an inadequate extent. In addition, due to the widening of the pull bands, and taking into account the aforementioned tension values, it becomes possible to match the longitudinal tension across the back approximately to the longitudinal tension across the breast. In the case of narrower pull bands the tension of the bands would have to be increased to an undesired extent to achieve the same effect.

Higher stretching values than those given, such as e.g. in the case of common knitwear in longitudinal direction, or in the case of wrapping bandages with only little or even no elasticity, would case the wearer of the bandage to be substantially obstructed in his movements, which however would impede the healing process. The patient would also only ungladly put on the bandage, so that the wearing of the bandage would be rather seldom.

Lower stretching values that those given, such as e.g. in the case of common knitwear in transverse direction, or also with highly-elastic corsetry or shoulder clothing, cause the wearer to feel a pull that is not gentle enough in a position that is unfavorable for the healing process as well, so that the bandage cannot be regarded as a "remainder bandage".

With the bandage according to the present invention is moreover preferred for the pull band to taper off toward the outside of the body and to be fastenable— eventually adjustably so—on the back part, preferably on the side seam beneath the shoulder. Namely, every pull band transmits pull forces to the back part, and provision is therefore to be made that these forces are accepted optimally without resulting in unpleasant folds. In that in this process the pull band forms the spade itself, the forces are transmitted not only in the longitudinal direction of the band, but also laterally to the shoulder joint of the wearer, whereby not only high strength is obtained, but the supporting effect in the region of the shoulder joint is also improved.

Because of the forces to be accepted it is beneficial for the pull bands to consist of reinforced or two-layered material, especially of knitwear. The reinforcement can naturally also be accomplished by a corresponding material selection. Knitwear is especially preferred because, as is known, it has a certain inherent elasticity. Just in this case it is however of advantage for the edges of the pull bands to be hemmed with trim bands, since on the one hand knitwear does not have its own selvedge, and on the other hand making the selvedge by the welding of plastic material would involve a sacrifice of elasticity. Such trim bands could consist of obliquely woven bands (i.e. woven ribbons with threads extending oblique to the longitudinal axis) or they can also preferably consist of knitwear.

For the supporting function it is as such adequate for the back part to correspond to an at least nearly rectangular strip between the shoulder joints, but for the purpose of performing an additional function it can also have the form of a part of a piece of clothing, and hence of a shirt or vest.

Otherwise, it is especially expedient for the bandage to be connected, eventually releasably, with an inside and/or outside shirt. The connection of the reinforcing part with the shirt-like piece of clothing can be relatively loose, (it is also possible for no connection to be provided at all), and it is expediently releasable.

In such a configuration the inside shirt or undershirt constitutes a cushioning underlayment, which is especially advantageous if in the simplest case the pull bands are connected by tying in the manner of apron strings. Conversely, the outside shirt or undershirt covers the bandage such that it does not exert pressure, or does so only to a slight extent, on the outer garments.

The entire support clothing takes on an agreeable appearance if the shirt-like piece of clothing consists of two layers, between which the shoulder bandage according to the present invention is arranged, in which case it is expediently connected at least with the underlying inside layer by short sections of seams at the beginning and end of the shoulder seam and/or the side seam under the shoulder. Then the shoulder bandage is also secured well against slipping.

However, with this covering the access to the pull bands to be fastened or adjusted behind the back of the wearer is facilitated for another person if the outer layer has at least one opening for reaching through to the ends of the pull bands to be fastened on the back. This opening can be provided by leaving a section of the waist seam between the inside and outside shirt open, or by openings in the area of both side seams beneath the shoulders, or also by separate opening slots, for example if the upper part that is connected with the reinforcement part is laid over the underpart of the piece of clothing in the manner of a trenchcoat, a slit being left free between them.

For the supporting function, while simultaneously assuring that the wearer retains his full freedom of movement it is especially important for the material of the supporting clothing to be reversibly stretchable according to the aforementioned values, the stretched material recovering to the extent possible fully elastically when the pull tension is released.

EXAMPLE

Four spools of a 40-gauge yarn (40,000 meters of yarn per kg) of 85% polyvinyl chloride fibers and 15% polyacryl nitrile fibers, four spools of a covered elastomer yarn and two spools of the same elastomer yarn as an inlay thread. This thread consists of 42% polyurethane elastomer (dtex 156) and 58% covering of texturized polyamide 66 (dtex 44/13/1) by weight. It has a stretching capacity of 280% and—with a preload of 0.5 g.—a running length of 48,000 m per kg. A fabric with e.g. 98% recovery of stretching in longitudinal direction is obtained. The preload is adjusted such that only 8.5% elastomer is contained in the end product; the remaining components are 62.3% polyvinyl chloride, 11.0% polyacryl nitrile and 18.2% polyamide. The material has a reversible elongation of 72% with a stressing of 2.5 kg/100 mm.

The stretching and its reversibility in transverse direction are governed by the type of knit. Normally, an adequate reversal is obtained only after washing, insofar as a corresponding stretchability and recoverability was not imparted to the material by the inclusion of a rubber thread in the transverse direction (hence, on circular knitting machines quasi-spirally). It is therefore preferred for the back part and/or the pull bands to be placed with their longitudinal direction transversely across the back. The material should have a reversible stretch of at least 10%, preferably of at least 40%.

It has proven to be of special advantage to provide a cushioning between the pull band, or at least between its edges on the one hand and the front side of the shoulder joint on the other hand, on which the pull is exerted. This can be e.g. a layer of a actively breathing foam plastic that is either placed over the respective length of the pull band or—since the foam plastic might impair the elastic stretch of the pull band—better fastened to the inside shirt, e.g. sewn in with the aid of a covering of a similar material.

Figure 1:
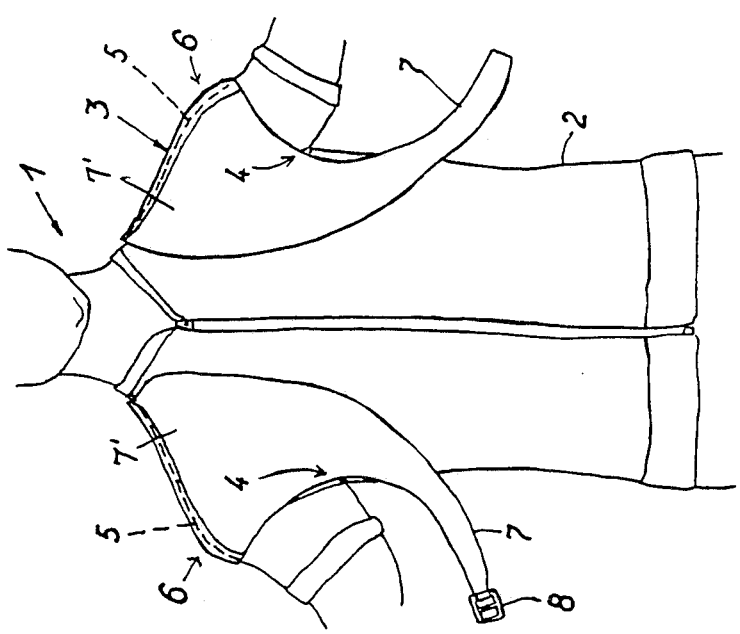

Further details ensue on the basis of the following description of examples of embodiments shown schematically in the drawing. Shown are:

FIG. 1 a front view of a first embodiment of the shoulder bandage according to the present invention after it has been put on, but before the two pull bands are connected;

FIG. 1A a rear view of the same embodiment after the connection of the two pull bands;

FIG. 2 a further embodiment in a representation similar to that of FIG. 1; and

FIG. 2A latter embodiment in a view analogous to that of FIG. 1A.

According to FIG. 1 a person 1 to be treated therapeutically has put on a shoulder bandage 3 over an inside shirt 2. By a curved shoulder seam 5 the shoulder bandage forms a spade 6 enclosing each of the shoulder joints 4 of the person 1. The spade thereby encloses the shoulder joint 4 on several sides. Hence the elasticity of the shoulder bandage 3 provides multi-sided supporting action in the region of the shoulder joint 4.

A pull band 7 that is relatively wide in its upper area 7' extends from each shoulder seam 5 to split up the pulling forces over a large section of the seam 5, while the pull bands taper off toward their free ends 7. As can be seen, the two pull bands 7 are tailored with a curvature such that normally their free ends point toward the outside of the body. It is thereby possible to pass them underneath the shoulder 4 of the wearer 1 without being folded, and to fasten them behind his back. For such fastening the end of one of the pull bands can be fitted with a buckle 8.

The inside shirt 2 can eventually constitute part of the supporting piece of clothing by being connected with the shoulder bandage 3 by the shoulder seam 5. In order to conceal the pull bands 7, a similar shirt 10 that is eventually connected with the inside shirt 2 and/or the shoulder bandage 3 can be pulled over as an outside layer. This connection can be made e.g. by means of a zipper or press buttons to enable the outside shirt to be washed separate. As such it would be possible to connect the inside shirt and the outside shirt with the shoulder bandage 3 over the entire shoulder seam, but it is preferred for the connection to be made only by short sections of the seam at the beginning and end of the shoulder seam 5 and/or of the side seam 12 under the shoulder 4.

It has, by the way, in contrast to the schematic representation in the drawing, proven to be advantageous for the front sides of the inside and/or outside shirt (2, 10) not to be high-necked, but to have a low-cut V-neck, especially for women, so that the breast is not subjected to unpleasant pressure by the still relatively stiffly fitting piece of clothing. Just in the case of women it may moreover be desirable to limit the length of these pieces of clothing at the waist, and hence at the narrowest part, to assure a good fit and to avoid upward slipping; conversely, for men a longer cut that extends over an eventual paunch may be more appropriate.

In FIG. 1A the situation after the connection of the two pull bands 7 behind the back of the wearer 1 is shown. By virtue of this connection a pull in the region between the shoulder blades ensues that provides for a straight posture of the wearer 1. It can be seen that the back part 9 of the shoulder bandage 3 beneath the spades 6 is nearly rectangular.

If the inside shirt 2 is foregone, or if it is separated from the shoulder bandage proper 2, the back part 9 with its share in the spades also plays the part of the piece of clothing that provides a firm grip for the pull bands 7. If the shoulder bandage 3 is however connected with the inside shirt 2 so that this is the part that the wearer 1 puts on, the back part 9 with the spades 6 plays *only* the part of a reinforcing element, the function of which is to accept the pull of the pull bands 7.

As already mentioned the shoulder bandage 3 can be covered by an outside layer or an outside shirt 10 (insinuated by a dot-dash line). In this case another person making or altering the connection of the free ends of the pull bands 7 by means of the buckle 8 could only find access to the buckle 8 by lifting the outside shirt 10. To facilitate such manipulation the waist seam 14 between the inside and outside shirts on the back is interrupted over a section of its length, or a slit 11 is provided in the outside shirt.

For the two pull band 7 a reinforcement is advantageous because it is their function to accept the tensioning forces. They consist e.g. of two layers, or a reinforcement is provided by means of the material selection. In addition, however, a high elasticity with a stretching ability of 25% to 60%, preferably of about 40%, especially in the transverse direction of the back part 9, but also for the pull bands 7, is advantageous; for this reason not only is an elastic thread material such as crimped yarn of PVC and/or acryl fibers which also provide a favorable friction electricity that promotes the circulation used; a fabric is expediently made out of this fiber material in the form of knitwear which, as is known, possesses a certain inherent elasticity. Just for this case however it is important to provide a hem made expediently with the aid of elastic trim ribbons 13.

The trim ribbons 13 expendiently edge the entire shoulder bandage 3. To be taken into account is that every pull band 7 can conist of 2 layers, but that for the back part 9 this is generally not only not required, but for the purpose of avoiding unpleasant feeling of hotness and sweating it is sometimes even inexpedient. Hence, the two-layer or reinforced material of the pull bands preferably ends at the shoulder seam 5.

FIG. 2 shows an embodiment in which the back part 9 itself is integrated in the inside shirt 102, at the shoulder seam 104 of which the pull bands 7 are sewn on directly. Hence, here only the inside shirt 102 envelops the shoulder joints 6, and it is apparent that such an embodiment does effect a stiffening and supporting of the spinal column by the connection of the two pull band ends 208 behind the back of the wearer 1 that is then made; however, the supporting effect in the region of the shoulder joint spades 6 of the wearer 1 naturally remains slighter.

On the basis of FIG. 2A it can also be seen that the connection of the free ends of the pull bands need not necessarily be connected directly together, but that corresponding connection fixtures 208 can be arranged on the back part 109, here in the form of press buttons and Velco closure straps, the mating part of each being provided at the ends of the pull bands 7. For improved acceptance of the forces it can be advantageous to integrate a reinforcing part 16 insinuated by a dot-dash line in the piece of clothing 102 between the two free ends of the pull bands 7.

It is especially preferred for the connecting fixtures 208 not to be attached on the back of the wearer 1, upon which they will bear and be unpleasantly felt when leaned thereupon, but at the side seam under the shoulder 4. Better than press buttons or Velco closer straps, which might eventually not withstand a strong pull, is also the connection by means of hooks and eyes.

Various possibilities of variation ensue in the scope of the invention; for example for rheumatic shoulder joint afflictions it can be expedient to exert not only a supporting function, but to use especially warm fiber material such as Angora wool as well, or at least to mix it in with the material of the shoulder bandage and/or of the inside or outside shirt. Especially advantageous however is—at least for the layers lying immediately against the skin of the wearer—the use of plastic fibers that generate friction electricity on the skin, thereby promoting the circulation.

I claim:

1. A shoulder bandage comprising a back part for covering a substantial portion of the upper back of the user, said back part including an upper edge having spaced apart portions for disposition on opposite sides of the neck of a user, each said portion having a pull band extending therefrom in a forward direction when said shoulder bandage is placed on a user, each said pull band having a length permitting each band to extend over the front side of the shoulder joint of a user and under the shoulder around to said back part, each said pull band having a free end and said back part having means for fastening said free ends of said pull bands to said back part, said pull bands being made of elastic material having a pull back force of approximately 3.92 to about 11.77 Newtons with a 10% stretching on a 5 centimeter wide by 10 centimeter long band portion at a displacement rate of 5 centimeters per minute measured transversely across the back and longitudinally across each said pull band and a pull back force of about 1.96 to about 4.9 Newtons measured on the 5 centimeter wide by 10 centimeter long pull band portion with a 10% stretching and a displacement rate of 5 centimeters per minute measured longitudinally across the back part and transversely across the pull bands.

2. The shoulder bandage as claimed in claim 1 wherein a pullback force is provided for each said pull band of about 4.9 to about 7.85 Newtons measured on a 5 centimeter wide and 10 centimeter long portion of a said band under 10% stretching with a displacement rate of 5 centimeters per minute measured transversely across said back part and longitudinally across said respective pull bands and a pull back force of about 2.94 Newtons to about 3.92 Newtons measured on a 5 centimeter wide and 10 centimeter long portion of the said respective pull bands under 10% stretching with a displacement rate of 5 centimeters per minute measured longitudinally across the back part and transversely across said respective pull band.

3. The bandage as claimed in claim 1 wherein the pull bands comprise reinforced fabric having edges hemmed with trim bands of foam plastic.

4. The bandage as claimed in claim 1 wherein said bandage is connected releasably with an inside shirt, the connection being made by a short section of seam in the area of the shoulder seam.

5. The bandage as claimed in claim 1 wherein said bandage is connected releasably with an outside shirt, the connection being made by a short section of seam in the area of said shoulder seam.

6. The bandage as claimed in claim 1 wherein said back part constitutes part of a shirt.

7. The bandage as claimed in claim 1 wherein said back part comprises a portion of a vest.

8. The bandage as claimed in claim 1, wherein a shoulder conforming part (6) is provided to cover the lateral clavicula and at the level of the acromio-clavicular joint with the pull bands (7).

9. Bandage as claimed in claim 1, wherein the pull band (7) is tailored tapering away from the body and is fastenable adjustably on the back part (9, 109), at the side seam (12) under the shoulder (4).

10. Bandage as claimed in claim 1, wherein the pull bands (7) comprises reinforced fabric, especially of knitwear, their edges preferably being hemmed with trim bands (13) and the pull bands having a cushioning underlayment.

11. The bandage as claimed in claim 14 wherein said outside shirt is provided with a waist seam with said waist seam including a slit.

12. Bandage as claimed in claim 8, wherein the back part (9, 109) extends up to the shoulder seam (5, 104), the pull band (7) preferably being widened in its region of attachment (7') to the width of the shoulder seam (5, 104).

13. Bandage as claimed in claim 12, wherein at least a part of the pull band (7) itself makes up a part of the shoulder-conforming part (6).

* * * * *